United States Patent [19]  [11] 4,328,217
Gabby et al.  [45] May 4, 1982

[54] BRAN TABLET COMPOSITION AND PROCESS

[75] Inventors: John L. Gabby; Gerald K. Ashby; Dennis W. Cameron; Richard C. Theuer, all of Evansville, Ind.

[73] Assignee: Mead Johnson & Company, Evansville, Ind.

[21] Appl. No.: 564,409

[22] Filed: Apr. 2, 1975

Related U.S. Application Data

[63] Continuation of Ser. No. 450,539, Mar. 12, 1974, abandoned, which is a continuation-in-part of Ser. No. 319,252, Dec. 29, 1972, abandoned.

[51] Int. Cl.³ .................... A61K 35/78; A61K 33/42; A61K 33/10; A61K 31/70
[52] U.S. Cl. .................................. 424/195; 424/128; 424/156; 424/180
[58] Field of Search ................ 424/128, 195, 156, 180

[56] References Cited

U.S. PATENT DOCUMENTS

| | | | |
|---|---|---|---|
| 1,189,133 | 6/1916 | Kellogg | 99/83 |
| 1,382,963 | 6/1921 | Ellis | 99/83 |
| 2,075,846 | 4/1937 | Halliday | 99/83 |
| 2,509,449 | 5/1950 | Raymer et al. | 99/83 |

FOREIGN PATENT DOCUMENTS

| | | | |
|---|---|---|---|
| 12484 | 3/1929 | Australia | 426/454 |
| 7986 | of 1888 | United Kingdom | 426/454 |

OTHER PUBLICATIONS

*Remington's Practice of Pharmacy*, Martin et al., 125 Ed.; Mack Pub. Co., Easton, Penna/1961—pp. 446–447.
*Chemical Abstracts*, vol. 61, 11252, (1964).
Martin II—Husa's Pharmaceutical Dispensing 6th Ed., Mack Pub. Co. Easton, Pa., 1966.
Prevention, Jan. 1972, Rodate Presp., Inc., Emmaus, Pa., pp. 18, 49 and 50.7n A bran tablet unit dosage form composition employing comminuted bran useful as a bulk cathartic agent is provided. The bran tablet compositions have suitable characteristics with respect to handling and packaging procedures and are substantially more palatable than whole bran.

*Primary Examiner*—Frederick E. Waddell
*Attorney, Agent, or Firm*—Robert H. Uloth; Irving Holtzman

[57] ABSTRACT

A bran tablet unit dosage form composition employing comminuted bran useful as a bulk cathartic agent is provided. The bran tablet compositions have suitable characteristics with respect to handling and packaging procedures and are substantially more palatable than whole bran.

6 Claims, No Drawings

BRAN TABLET COMPOSITION AND PROCESS

CROSS-REFERENCE TO RELATED APPLICATIONS

This patent application is a continuation of application Ser. No. 450,539, filed Mar. 12, 1974, now abandoned, which is a continuation-in-part of pending U.S. patent application Ser. No. 319,252 filed Dec. 29, 1972, now abandoned.

BACKGROUND OF THE INVENTION

Bran is considered to be bulk-producing laxative which stimulates reflux peristalsis by increasing intestinal contents. This invention pertains to bran compositions and, more particularly, relates to bran compositions useful in the treatment of diverticular disease and constipation.

It has long been known that bran is of value as a bulk cathartic. With respect to the state of the art, the following references are illustrative. U.S. Pat. No. 366,992 issued in 1887 teaches that a baked confection consisting of bran and a gumdrop material produce great regularity of the bowels. *Drugs of Choice* (1970–1971) (C. V. Mosby Co., St. Louis) in the section on "Drugs for Gastrointestinal Diseases, page 320" indicate that a bulk producing agent such as bran is useful in keeping stools soft in patients with diverticulitis and constipation and in providing bulk to the stools of patients with an ileostomy or colostomy. N. S. Painter and D. P. Burkitt, *British Medical Journal*, 22, 453 (May, 1971) report that a diet containing bran relieved or abolished abdominal pain and distension in over 80% of patients having symptoms of diverticular disease. There remains some uncertainty whether a high-bran diet prevents diverticulitis but, nevertheless, the symptoms of diverticulosis are usually diminished or abolished by adding bran to the diet.

Patients with diverticular disease or constipation have been advised by Painter, *Disease-A-Month*, page 52, June, 1970 to take 1 to 2 teaspoons of unprocessed bran three times a day or, if this is not sufficient to produce softening of stools, to increase the amount to several tablespoons per day. One teaspon of unprocessed bran weighs roughly 1 g. while a tablespoon weighs about 3 g. The consumption of the suggested quantity of bran for the foregoing purpose presents considerable difficulty and inconvenience to the patient. For instance, it is recognized that bran tastes much like sawdust and is, therefore, decidedly unpalatable. In fact, Painter, supra, has suggested that when using bran in a high residue diet, the bran should be washed down with water, fruit juice, milk or mixed with soup or with flour for baking in order to mask the unpleasant taste. Aside from unpalatability, another aspect of using unprocessed bran as a high residue diet is the inconvenience involved in carrying about bulk bran when traveling as well as the personal embarrassment experienced by some individuals on consuming bulk bran according to Painter, supra, when eating in public places. Another significant disadvantage is the problem of regulating the dosage of whole bran which is determined to a large extent by volume and may vary on a weight basis according to the size of the granules of the various cereal grain brans.

SUMMARY OF THE INVENTION

It is an object of the present invention to provide a bran tablet composition in pharmaceutical unit dosage form useful as a bulk laxative.

A further object is to provide a bran tablet composition useful in the treatment of gastrointestinal problems such as constipation and diverticular disease.

A still further object is to provide a bran tablet composition which is palatable.

A still further object is the provision of a pharmaceutical bran tablet composition in dosage unit form which can be consumed in a reproducible manner to produce a bulk-laxative effect.

Yet another object is the provision of an economical and reproducible process for the production of bran tablet compositions which is adapted to commercial use.

These and other objectives will be obvious in light of the description of the invention which follows.

According to one broad form of the present invention a bran composition is provided which is characterized as containing by weight from 20% to 70% comminuted bran solids; from 30% to 80% sugar; from 0% to 8% of a binding agent such as gelatin, pregelatinized starch, acacia, polyvinylpyrrolidone, methyl cellulose, zein and the like; from 0% to 2% excipients such as magnesium stearate and colloidal silicon dioxide; from 0% to 15% tableting adjuvants such as calcium carbonate or dibasic calcium phosphate and from 1% to 5% water. A preferred form of bran composition comprises 42% to 47% comminuted bran solids (equivalent to about 47% to 53% bran), 46% to 51% sucrose, 4% to 5% gelatin, 0% to 3% calcium carbonate and from 2% to 4% water. Another preferred form bran tablet composition comprises from 38% to 51% comminuted bran solids (equivalent to about 42% to 57% bran), 31% to 51% sucrose, 3% to 6% pregelatinized starch, 10% to 15% dibasic calcium phosphate and from 2% to 4% water. Still another preferred bran tablet composition comprises 50% comminuted bran, 6.5% pregelatinized starch, 15.0% lactose, 27.5% sucrose, 0.1% magnesium stearate and 0.9% colloidal silicon dioxide. The bran compositions of the present invention may be fortified with various vitamins and minerals to the extent of satisfying the daily minimum requirements recommended by the Food and Nutrition Board of the National Academy of Sciences—National Research Council, Publication 1694, revised 1968, "Recommended dietary allowance".

Particularly preferred unit dosage forms comprise a tablet containing 400–500 mg. of comminuted bran solids, 450–550 mg. of sucrose, 20–40 mg. of gelatin and 5–25 mg. of calcium carbonate; and a tablet containing 1600–2000 mg. of comminuted bran solids; 1500–1900 mg. of sucrose, 150–250 mg. of pregelatinized starch and 500–700 mg. of dibasic calcium phosphate.

Another preferred unit dosage form comprises a tablet containing 1000 mg. of comminuted bran, 130 mg. of pregelatinized starch, 300 mg. lactose, 550 mg. sucrose, 2 mg. magnesium stearate and 18 mg. colloidal silicon dioxide.

For the purpose of this invention, bran is defined as the broken hull of the seed of a cereal grain separated from the flour or meal and includes the bran of cereal grains such as rye, oats, maize, rice and wheat, of which the most preferred is wheat. Bran contains varying amounts of water, depending upon atmospheric humidity and temperature. *Agricultural Handbook No. 8*, published by the Agriculture Research Service, United States Department of Agriculture, establishes that commercially milled wheat bran may contain 11.5% water while a value of 9.7% is given for rice bran. It is to be understood that, as used herein, the term "bran solids" refers to essentially anhydrous bran whereas "bran" refers to that containing significant moisture (e.g., from 3-15%).

The term "sugar" as used herein, includes a saccharide selected from the group consisting of sucrose, fructose, maltose, lactose, and dextrose, of which the most preferred is lactose and sucrose. Broadly, the term "sugar" is intended to refer to saccharides which are sweet to the taste, edible, and available in pulverulent form.

The term "pregelatinized starch" as used herein, refers to partially hydrolyzed starches prepared according to *Starch: Chemistry and Technology*, Vol. II, E. L. Powell, Chapter XXII (Academic Press, 1967). Examples of commercially available pregelatinized starches are Amijel ® and the Fro-Dex ® corn syrup solids.

A pharmaceutical composition in dosage unit form of the present invention is obtained according to another aspect of the present invention by a process which comprises comminuting unprocessed bran; mixing the comminuted bran with sugar-syrup until a uniform wet mix is obtained; extruding the wet mix through a suitable extruder; drying the extruded wet mix to provide a dry mix; grinding the dry mix to provide a granulated mix; and tableting the dry granulated mix to provide tablets containing up to 70% bran and of sufficient hardness to withstand routine packaging and handling procedures. The comminuted bran can be blended with suitable tablet excipients, fillers and binding agents (e.g., gelatin, pregelatinized starch, calcium carbonate, dibasic calcium phosphate) prior to mixing with sugar-syrup if desired.

The extruding step is critical to obtaining bran tablet composition in that harder tablets are obtained from extruded wet mix than from non-extruded. Screw-type extruders such as the Ambrette or ECK model EXPC-100 (Elanco Products, Indianapolis, Indiana) fitted with extrusion plates having openings of about 1-3 mm. are particularly useful.

With respect to comminuting unprocessed bran, a hammer mill employing air separation and air flow of process material such as a Schutz-O'Neil air swept pulverizer is satisfactory. High speed hammer mills, for example, a Fitzmill comminuting machine or an impact type such as a Mikro-Pulverizor, are also useful provided the unprocessed bran is first blended with at least 33% (preferably 50%) by weight of Dry ice (solid carbon dioxide) in order to provide frangible bran particles. If the unprocessed bran is not blended with Dry ice, the bran has a tendency to gum and clog the milling chamber.

In connection with blending the unprocessed bran with Dry ice, a rapid high efficiency solids-solids blending machine such as a Lodige mixer is satisfactory. The Lodige mixer consists of a cylindrical shell equipped with a series of plow-shaped mixing tools and a high speed blender chopper assembly mounted at the bottom rear of the mixer.

After the unprocessed bran is comminuted, it can be blended with tableting fillers and binders if desired and then mixed with sugar-syrup. Blending and mixing can be carried out in a Lodige type mixer or a heavy duty sigma arm stirrer to provide a wet mix. The wet mix is extruded through a screw-type extruder, for example, an Ambrette or ECK model EXPC-100, fitted with a suitable extrusion plate (preferably 2 mm.), dried and then granulated in a hammer mill (e.g., a Fitzmill) to provide a granulated mix which is tableted in standard tableting machines.

As stated herein, one preferred aspect of the present invention is based upon the discovery that a mixture of comminuted bran and sugar extruded under pressure according to the process of the present invention provides an extrudate which can be pressed into tablets of sufficient hardness to withstand conditions encountered in normal packaging and handling without undue breakage. The bran tablets are substantially more platable than unprocessed bran and have a rather pleasant bitter-sweet taste.

Characteristics of the bran tablet unit dosage forms of the present invention with respect to hardness can be measured by the Strong Cobb Arner Hardness Tester (Strong Cobb Arner, Inc., Cleveland, Ohio 44120) for compressed tablets. This instrument consists of a piston operated by air pressure connected to a standardized gauge for registering the air pressure required to fracture the tablet. Five tablets are generally employed in a standardized test wherein the sum of the units from the gauge readings for each fractured tablet is divided by the number of tablets to afford an average tablet hardness in Strong Cobb Units (hereinafter identified as "S.C.U."). Tablets prepared according to the process of the present invention wherein the wet bran mix is extruded have S.C.U. tablet hardness of 18-26. When the extrusion step is omitted, the tablets are not as hard and have S.C.U. values of about 8-15. Tablets with a low S.C.U. value are more susceptible to breakage in routine packaging and handling procedures.

S.C.U. values are given in the following table for tablets prepared from a representative bran composition of the instant invention comprised proportionally of comminuted wheat bran equivalent to 44,250 g. of bran solids; 31,995 g. of granulated sucrose; 16,600 g. of powdered sucrose; 3,000 g. of gelatin; 1,500 g. of calcium carbonate and 24,000 g. of distilled water combined according to the process of the present invention but varying the time and mixing speed in a sigma arm stirrer or omitting the extrusion step. Each tablet weighs 1.0 g. and contains 442.5 mg. of comminuted bran solids, 486 mg. of sucrose, 30 mg. of gelatin and 15 mg. of calcium carbonate.

TABLE I

| | HARDNESS OF BRAN TABLETS (Strong Cobb Units) | | |
|---|---|---|---|
| Mixing Time | Speed | Extruder | S.C.U. |
| 30 min. | slow | None | 10 |
| 7 hr. | slow | None | 13-16 |
| 30 min. | fast | None | 19 |
| 30 min. | slow | Ambrette (5/64 inch plate) | 22 |

In the above comparison, the 30 min. and 7 hr. mixing time illustrates that the degree of hardness (S.C.U.) of the bran tablet composition of the present invention is proportionally related to the length of the stirring period in a sigma arm stirrer. Extending the stirring time beyond 7 hr. would probably provide tablets of sufficient hardness but would be impractical and economically unfavorable from a manufacturing viewpoint. A tablet having a suitable hardness characteristic is provided by fast speed stirring for 30 min. However, in view of the unusually heavy consistency of the bran composition mix, stirring at the required "fast" speed is also impractical from a manufacturing viewpoint.

The comminuted bran tablet composition of the present invention is an effective bulk forming cathartic agent. Comparison of a group of rats fed a basal diet supplemented with bran tablets with a group of rats fed a similar diet but with no bran tablet supplement indicated that the bran tablet group had a three-fold increase in total fecal weight. Administration of a dose of from 2 to 4 one gram tablets three times daily to patients suffering from constipation was generally judged to be acceptable or highly acceptable in promoting normal bowel movements.

The following specific examples illustrate the pulverized bran tablet compositions of the present invention and the novel process employed in preparation thereof.

EXAMPLE 1

Bran-sucrose-gelatin-calcium carbonate composition

Gelatin-sucrose syrup is prepared by placing the following ingredients in a mixing kettle equipped with a heater and agitator.

| | |
|---|---|
| Distilled Water | 24,000.0 g. |
| Gelatin | 3,000.0 g. |
| Sucrose, Granular | 31,995.0 g. |

The mixture is heated up to about 150° F. with agitation until solution is effected and the gelatin-sucrose syrup then slowly stirred and held at a temperature of about 150° F. until needed.

Wheat bran is comminuted in a Schutz-O'Neill Air-swept Pulverizer to provide a particle size whereby a minimum of 94% passes through a United States Standard number 20 mesh screen and a maximum of 60% passes through a United States Standard number 80 mesh screen. The required amount of bran for the batch is calculated by the formula: $44250 \text{ g.} \times 100 \div 100 - \%$ moisture in bran. After pulverizing, the bran is transferred to a heavy-duty double sigma arm mixer and mixed with 1,500 g. of calcium carbonate, and the previously prepared gelatin-sucrose syrup added rapidly thereto with stirring. When the bran appears to be damp, the mixture is stirred for a 30 minute period and then stopped. Powdered sucrose (16,600.0 g.) is added and the mixture agitated for an additional 2 to 5 minutes. The wet mix is then discharged through an Ambrette screw extruder and the extrudate spread on drying trays and dried in an oven at 225° F. to 3% moisture content. The dried extrudate is granulated employing a Fitzmill (2A plate) and then pressed into 1.0 g. tablets by a conventional tableting machine.

There is obtained by this process about 100,000 one gram tablets with each tablet providing wheat bran solids equivalent to 500 mg. of wheat bran. On a dry weight (percent) basis each bran tablet contains 442.5 mg. (44.3%) of pulverized bran solids, 486 mg. (48.6%) of sucrose, 30 mg. (3.0%) of gelatin and 15 mg. (1.5%) of calcium carbonate. Bran tablets prepared according to the above process have a hardness value of 19 Strong-Cobb Units permitting packaging without excessive loss from crumbling and breaking.

EXAMPLE 2

Bran-sucrose-Amijel-dibasic calcium phosphate composition

Sucrose syrup is prepared by placing the following ingredients in a mixing kettle equipped with a heater and agitator.

| | |
|---|---|
| Distilled Water | 100,000.0 g. |
| Sucrose, granular | 170,184.5 g. |

The mixture is heated to about 150° F. with agitation until solution is effected and the sucrose syrup slowly stirred and held at a temperature of about 150° F. until needed.

Equal weights of unprocessed wheat bran and Dry ice pellets are thoroughly mixed in a Lodige mixer for 1 minute and then permitted to stand for an additional 5 minutes. The blended wheat bran-dry ice material is passed through a Model M5K Mikro-Pulverizer, and the micropulverized material dried at 120° F. until all traces of dry ice disappear. The amount of "bran" equivalent to the desired weight of "bran solids" required for the batch is calculated by the formula: $177,000 \times 100 \div 100 - \%$ moisture in bran. The pulverized bran is mixed with 60,000 g. of dibasic calcium phosphate and 20,000 g. of Amijel in a Lodige mixer for 5 minutes at 130 rpm with choppers on and the previously prepared sucrose syrup solution then added. Mixing is continued until the wet mix has a soft spongy but not doughy texture. The wet mix is passed through an ECK model EXPC-100 extruder (Elanco Products, Indianapolis, Indiana) equipped with a 2 mm. plate and the extruded material dried at 225° F. to 3% moisture. The dried extrudate is granulated, employing a high speed hammer mill such as a Fitzpatrick comminuting machine (2A plate, knives forward) and compressed into flat face beveled edge tablets weighing 4.4 g. (including 3% moisture) by a conventional tableting machine. There is obtained by this process about 100,000 tablets with each tablet providing wheat bran solids equivalent to 2 g. of wheat bran. Tablets prepared in this manner have a hardness value of 22 Strong-Cobb Units and the composition as follows:

| | Mg. | Percent by Weight |
|---|---|---|
| Bran Solids | 1770 | 40.3 |
| Sucrose | 1702 | 38.6 |
| Amijel | 200 | 4.55 |
| Dibasic Calcium Phosphate | 600 | 13.7 |

If desired, the dried granulated extrudate can be pressed into tablets of various dosage unit form such as 1.1 g., 2.2 g., and 3.3 g. tablets containing 442.5 mg., 885 mg., and 1,327 mg. of wheat bran solids respectively as well as proportional amounts of sucrose, Amijel and dibasic calcium phosphate.

EXAMPLE 3

Comparison of extruded and non-extruded bran compositions

Comparison of the relative hardness of tablets obtained from extruded and non-extruded forms of the following bran compositions illustrate the importance of the "extrusion step" in the process of the present invention. The "extrusion step" was carried out with a screw-type ECK extruder equipped with a 2 mm. plate. All tablets contain approximately 3% moisture.

COMPOSITION A

| Ingredients | Grams | Percent in Tablet |
|---|---|---|
| Comminuted Wheat Bran Solids* | 13,280 | 44.3 |
| Calcium Carbonate | 450 | 1.5 |
| Sucrose powder | 4,980 | 16.7 |
| Sucrose granular | 9,000 | 30.0 |
| Amijel | 1,500 | 5.0 |
| Water (not retained) | 6,000 | — |

*Equivalent to 14,316 g. of bran containing 7.2% moisture.

Wet bran mix prepared in accordance with the procedure set forth in Example 2 with the exception that powdered sucrose was blended with the pulverized bran solids, calcium carbonate and Amijel prior to the addition of the sucrose syrup.

COMPOSITION B

| Ingredients | Grams | Percent in Tablet |
|---|---|---|
| Comminuted Wheat Bran Solids* | 13,280 | 46.3 |
| Calcium Carbonate | 450 | 1.6 |
| Sucrose Powder | 5,980 | 20.9 |
| Sucrose granular | 8,000 | 28.0 |
| Water (not retained) | 5,000 | — |

*Equivalent to 14,316 g. of bran containing 7.27% moisture.

Wet bran mix prepared in accordance with the procedure set forth in Example 2 with the exception that powdered sucrose was blended with the pulverized bran solids and calcium carbonate prior to the addition of the sucrose syrup.

COMPOSITION C

| Ingredients | Grams | Percent in Tablet |
|---|---|---|
| Comminuted Wheat Bran Solids* | 14,475 | 43.2 |
| Dibasic Calcium Phosphate | 4,500 | 13.5 |
| Sugar, granulated | 12,000 | 35.98 |
| Amijel | 1,500 | 4.5 |
| Water (not retained) | 6,000 | — |

*Equivalent to 15,000 g. of bran containing 3.51% moisture.

TABLE II
HARDNESS OF TABLETS IN STRONG-COBB UNITS

| COMPOSITION | EXTRUDED | NON-EXTRUDED |
|---|---|---|
| A | 22 | 16 |
| B | 24 | 16 |
| C | 24 | 19 |

EXAMPLE 4

Bran-Sucrose-Lactose-Pregelatinized Starch-Magnesium Stearate-Colloidal Silicon Dioxide Composition The following ingredients are employed in preparing a bran composition sufficient to make 20,000 two gram tablets containing 1,000 mg. of comminuted bran.

| Ingredients | Kilograms/20,000 Tablets |
|---|---|
| Comminuted wheat bran | 20.00 |
| Starch, pregelatinized | 2.60 |
| Lactose, hydrous spray process | 6.00 |
| Sucrose | 11.00 |
| Magnesium stearate | 0.04 |
| Colloidal silicon dioxide | 0.36 |

The comminuted wheat bran is preblended with lactose, pregelatinized starch, and about a 45% portion of the sucrose.

Hot (190° F.+or−10° F.) sucrose syrup solution is prepared from the remaining sucrose and added to the preblend mixture in a Ribbon Blender. After mixing for 10-15 min., the wet granulation is spread and dried at a temperature of 180°-200° F. for 3-5 hr. or until the moisture content of less than 2% is obtained. When drying is completed, the dried, cooled granulation is ground by passing through a Fitzpatrick comminutor using a No. 1 or No. 1524-0033 (0.033 inch opening) screen. The ground bran granulation is mixed with magnesium stearate and then compressed into 2 gram weight tablets using ⅜ inch flat bevelled edge punches.

Bran tablets provided by this process contain the following amounts of ingredients per tablet and have a hardness of 8 to 15 Strong Cobb Units.

| Ingredients | Mg./Tablet | Percent in Tablet |
|---|---|---|
| Comminuted wheat bran | 1,000.0 | 50.0 |
| Lactose | 300.0 | 15.0 |
| Pregelatinized starch | 130.0 | 6.5 |
| Sucrose | 550.0 | 27.5 |
| Magnesium stearate | 2.0 | 0.1 |
| Colloidal silicon dioxide, M-5 | 18.0 | 0.9 |

What is claimed is:

1. A process for preparing a pharmaceutical bran tablet for oral administration as a bulk cathartic agent comprising the steps of:
   mixing comminuted bran with that amount of sucrose syrup which provides a uniform wet mix which is damp in appearance;
   extruding the wet mix from a screw type extruder under pressure to provide a damp extrudate;
   drying the damp extrudate to provide a dry extrudate containing about 3% water;
   grinding the dry extrudate to provide a dry granulated mix; and
   tableting the dry granulated mix to provide tablets of sufficient hardness to withstand routine packaging and handling procedures.

2. The process of claim 1 wherein tablets are provided which contain up to 70% bran.

3. The process of claim 1 wherein unprocessed bran is comminuted to a particulate size so that a minimum of 94% passes through a number 20 mesh screen and a maximum of 60% passes through a number 80 mesh screen.

4. The process of claim 1 wherein comminuted bran is obtained by grinding in a hammer mill a blended mixture of unprocessed bran and solid carbon dioxide.

5. The process of claim 1 wherein fillers and binding agents selected from the group consisting of gelatin, pregelatinized starch, calcium carbonate and dibasic calcium phosphate are blended with the comminuted bran.

6. The process of claim 1 wherein the tablets produced have a hardness of 18-26 Strong Cobb Units.

* * * * *